United States Patent

Maruyama et al.

Patent Number: 5,997,902
Date of Patent: *Dec. 7, 1999

[54] RUMINAL DRUG DELIVERY DEVICE

[75] Inventors: Frederick H. Maruyama, San Jose; Judy A. Magruder, Mountain View, both of Calif.

[73] Assignee: Alza Corporation, Palo Alto, Calif.

[*] Notice: This patent is subject to a terminal disclaimer.

[21] Appl. No.: 09/127,552

[22] Filed: Aug. 3, 1998

Related U.S. Application Data

[62] Division of application No. 08/743,807, Nov. 5, 1996, Pat. No. 5,824,340, which is a division of application No. 08/475,916, Jun. 7, 1995, Pat. No. 5,639,477, which is a continuation-in-part of application No. 08/081,743, Jun. 23, 1993, Pat. No. 5,431,919.

[51] Int. Cl.[6] ......................................... A61K 9/24
[52] U.S. Cl. ............................... 424/473; 424/438
[58] Field of Search ..................... 424/473, 438

[56] References Cited

U.S. PATENT DOCUMENTS

| | | | |
|---|---|---|---|
| 4,595,583 | 6/1986 | Eckenhoff et al. | 424/15 |
| 4,612,186 | 9/1986 | Eckenhoff et al. | 424/15 |
| 4,772,474 | 9/1988 | Eckenhoff et al. | 424/465 |
| 4,844,984 | 7/1989 | Eckenhoff et al. | 424/438 |
| 4,872,873 | 10/1989 | Zingerman | 604/892.1 |
| 5,045,082 | 9/1991 | Ayer et al. | 604/892.1 |
| 5,122,128 | 6/1992 | Cardinal et al. | 604/890.1 |
| 5,206,024 | 4/1993 | Peery et al. | 424/438 |
| 5,213,809 | 5/1993 | Wright et al. | 424/473 |
| 5,431,919 | 7/1995 | Maruyama | 424/473 |

FOREIGN PATENT DOCUMENTS

WO90/11856  10/1990  WIPO.

Primary Examiner—Thurman K. Page
Assistant Examiner—Susan Tran
Attorney, Agent, or Firm—Mary Ann Dillahunty; Steven F. Stone; Pauline A. Clarke

[57] ABSTRACT

The present invention is concerned with improving the delivery of a drug from a ruminal delivery device to give a consistent delivery of drug to the ruminal environment. Thus, the invention is directed to an improved ruminal drug delivery device comprising a semipermeable membrane having an exit orifice and defining a compartment, the compartment containing a swellable osmotic agent expandable driving member, a drug to be dispensed, a density element and, optionally, a partition layer between the osmotic expandable driving member and the drug formulation, wherein the improvement comprises an essentially gas-impermeable barrier means that separates the density element from the other components within the delivery device for isolating gases evolved from the density element from the other components within the delivery device. The barrier means further includes a coupling to transfer osmotic pressure to the semipermeable wall. The invention is also directed to methods and articles for providing a consistent delivery of drug from a ruminal drug delivery device.

7 Claims, 5 Drawing Sheets

RUMINAL DRUG DELIVERY DEVICE

CROSS-REFERENCE TO COPENDING APPLICATIONS

This application is a divisional of application Ser. No. 08/743,807, filed Nov. 5, 1996 now U.S. Pat. No. 5,824,340, which is a division of Ser. No. 08/475,916 filed Jun. 7, 1995 now U.S. Pat. No. 5,639,419.

FIELD OF THE INVENTION

This invention relates to ruminal drug delivery devices. More particularly, this invention relates to a ruminal device having improved delivery activity.

BACKGROUND OF THE INVENTION

Ruminant animals, including cattle, sheep, giraffe, deer, goats, bison and camels, and more particularly cattle and sheep, comprise an important group of animals that require periodic administration of medicines, nutrients and other biologically active agents (which are hereinafter referred to in their broadest sense as "drugs") for the treatment and alleviation of various conditions and for better health.

Ruminants have a complex three or four compartment stomach, with the rumen being the largest compartment. The rumen serves as an important location for receiving and absorbing medicines and nutrients into other compartments including the abomasum and the intestine.

There are numerous ruminal delivery devices known in the art which are capable of prolongedly releasing drugs. These devices are easily swallowed by the ruminant or otherwise introduced into the rumen and remain within the rumen for a long period of time without being regurgitated or otherwise expelled. Typical devices having an osmotic portion which imbibes ruminal fluid and expands, forcing a liquid or paste drug portion of the device through an orifice into the rumen, are those disclosed in U.S. Pat. Nos. 4,595,583 and 4,612,186, the disclosures of which are incorporated herein by reference.

In order to insure that these devices remain in the rumen for a prolonged period of time, a density element is often incorporated into the device. Typically, the density element is manufactured from a material such as iron or steel, iron shot, iron shot coated with iron oxide, magnesium alloy, copper oxide or mixtures of cobalt oxide and iron powder, and the like. Such density elements typically have sufficient density to bring the overall density of the delivery device to a level greater than the density of ruminal fluid (approximately 1 gm/mL) and preferably to an overall density of at least 2 gm/mL.

The osmotic ruminal delivery device or bolus has encountered some difficulties, however. The daily output of the bolus has been seen to often be highly erratic. It has been found that density elements made from materials such as iron, magnesium or zinc are susceptible to corrosion in water or ruminal fluids. This corrosion causes production of gases, which gases enter into other portions of the device and accumulate as gas bubbles which can cause fissures within the drug formulation and/or the osmotic expandable driving member. The presence of such fissures can cause gaps in the flow of drug formulation or a rapid expulsion of a portion of the formulation. Typically, the formation of a fissure causes a rapid expulsion of a portion of the formulation (fissure/bubble formation) followed by gaps or a decrease in the flow of drug formulation (fissure closure or expulsion through orifice). Thus, erratic flow is observed with days of low output and days of high output. In one effort to decrease corrosion, density elements of sintered metal have been impregnated during manufacture with an inert hydrophobic material such as corn oil, silicone oil, mineral oil or wax (see, U.S. Pat. No. 5,206,024 and PCT patent publn. WO 90/11856). This method, while apparently successful, has the disadvantages of being a time-consuming process during, and adding considerable expense to, the manufacture of the ruminal delivery device. Additionally, this is not a practical solution when the density element is not of the fragmentable sintered type disclosed in the above publications.

Other difficulties arose with the use of the osmotic ruminal delivery devices. In some embodiments, the semipermeable wall is a cup defining a compartment, the cup having an open and an enclosed end. The interior diameter of the cup was sized to tightly fit the density element inserted within the compartment. A portion of the cup was crimped over to provide additional means to hold the density element within the cup. However, limitations in the configurations resulted in the release of the density element from the compartment.

SUMMARY OF THE INVENTION

The present invention is concerned with improving the delivery of a drug from a ruminal delivery device to give a consistent delivery of drug to the ruminal environment. Thus, the invention is directed to an improved ruminal drug delivery device comprising a semipermeable cup having an open end, a crimped portion adjacent the open end, and an exit orifice. The cup contains an osmotic expandable driving member, a drug to be dispensed, a density element and, optionally, a moveable partition layer between the osmotic expandable driving member and the drug formulation. An essentially gas-impermeable barrier means separates the density element from the other components within the delivery device to isolate gases evolved from the density element from the other components within the delivery device. According to the present invention, a coupling between the density element and the semipermeable cup reduces the stress applied to the crimped portion of the semipermeable cup. This provides additional means to retain the density element within the semipermeable cup.

This invention is also directed to an article which improves the performance of a ruminal drug delivery device. The article comprises an essentially gas-impermeable sleeve which is sized and shaped to be placed between the density element and the other components within the ruminal device. The sleeve surrounds and tightly engages the density element. The sleeve also acts as a barrier means to protect the drug formulation and other components from gas evolved during corrosion of the density element, thus providing a more constant and consistent delivery profile of drug from the device. Projections on the sleeve may engage with receiving depressions defined within the wall to act as a coupling to hold the density element within the compartment and alternatively, the sleeve may be directly bonded to the semipermeable wall.

DESCRIPTION OF THE TERMS

By the term "essentially impermeable" as used herein is meant that the barrier material is not permeable to such gases at all, or that the gases permeate the material in only a negligible amount, of no greater than about $20 \times 10^{-10}$ cm/sec-cmHg.

The term "drug" is used broadly and generically herein to refer to any drug or other beneficial agent which it is desired to deliver to a ruminant animal from a ruminal delivery device, and the present invention is not limited to any particular drugs. Such beneficial agents are known to the art and representative agents are disclosed in the patents incorporated herein by reference.

The expressions "exit means" as used herein are comprised of those means and methods suitable for releasing the product from the device under the pumping rate of the device. The expression includes an aperture, orifice, bore, stainless steel needles, hollow cellulose acetate tubes, polyolefin tube, capillary tube suitable for passing the agent, tube and conduits of various inside diameters, closed passageways containing a bioerodible material that erodes in the environment of use to produce an open passageway. Typical bicerodible materials include erodible polyglycolic and polylactic fibers, erodible gelatinous filaments, polyvinyl alcohol, and the like.

DETAILED DESCRIPTION OF THE INVENTION

Figure 1:
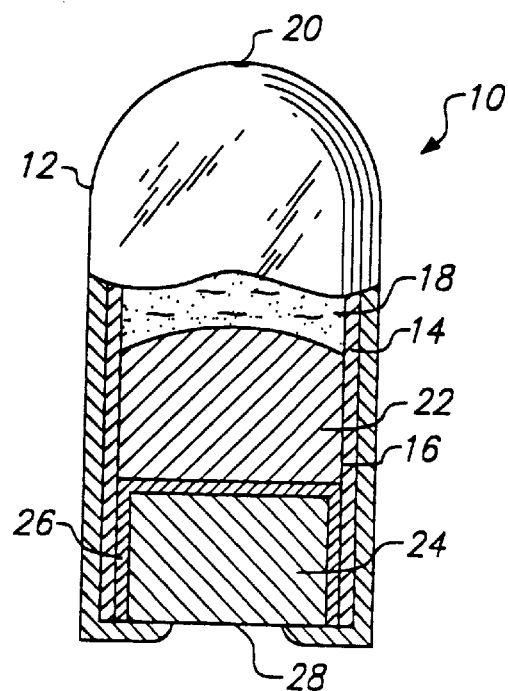
FIG. 1 is a partial cross-sectional view of one embodiment of an improved ruminal delivery device and barrier means according to the present invention.

It has been found that placing a barrier between the density element and the other components of a ruminal delivery device as generally disclosed herein substantially reduces erratic delivery of drug from the device, while at the same time being simple and inexpensive to incorporate into the manufacture of the device. It has also been found that providing means for coupling the density element to the semipermeable cup reduces the incidence of the density element being expelled from the device and into the environment of use.

The improved controlled release ruminal delivery device of this invention comprises a semipermeable membrane which defines a compartment, the compartment being divided into first and second portions by an interface or, in certain embodiments, by a moveable partition. The first compartment portion contains a swellable osmotic material and the second compartment portion contains a drug or medicament or other therapeutic agent to be dispensed, generally in a semiliquid, gel or paste form. A density element resides within the compartment and may be positioned either adjacent to the exit orifice or at the end opposite from the exit orifice or elsewhere in the device. An orifice having an inside cross-sectional shape and extending through the membrane and, when the density element is adjacent to the orifice, through the density element, connects the second compartment portion with the exterior of the device. When the device is in contact with water such as is found in the ruminal fluid of a ruminant, the semipermeable membrane allows water to pass therethrough which is imbibed by the swellable osmotic material which forces the interface between the osmotic material and the medicament to move the medicament to be dispensed through the orifice.

According to this invention, a gas barrier means which is placed between the density element and the other components within the device to separate the density element from the other components. The barrier means is essentially impermeable to gases that are evolved as a result of corrosion of materials making up the density element and acts to keep any such gases from passing into the other components, and especially the drug formulation, within the device. In addition, coupling means may be used for engaging the density element with the semipermeable membrane. This prevents the density element from being expelled from the device.

This invention will be described with respect to ruminal delivery devices of the type shown in the Figures, but it is not limited to the specific devices disclosed. The ruminal delivery device designs illustrated herein are merely exemplary of devices known to the art, and the gas barrier means of this invention can be adapted to fit in a ruminal delivery device and with a density element of any configuration. In the following description of the Figures, the Figures are not necessarily drawn to scale and like elements in the different Figures will be referred to by the same number.

FIG. 1 illustrates a ruminal device 10 having a semipermeable cup 12 which surrounds an optional internal capsule wall 14 and defines an internal compartment 16, which is partially shown in FIG. 1. The agent or drug to be delivered can be dispersed throughout a drug composition 18, which is delivered through an exit orifice 20 by pressure exerted upon said composition by an osmotically activated expandable driving member 22. A density element 24 is situated at the end of the device 10 opposite from the exit orifice 20. Present between density element 24 and expandable driving member 22 is a gas-impermeable barrier means 26 for keeping gas evolved as a result of corrosion of the density element from entering into the expandable driving member 22 and the drug formulation 18. That portion of density element 24 facing to the lower or bottom end 28 of device 10 is not enclosed by cup 12 or barrier means 26, in part so that the evolved gases can vent to the exterior environment.

Figure 2:
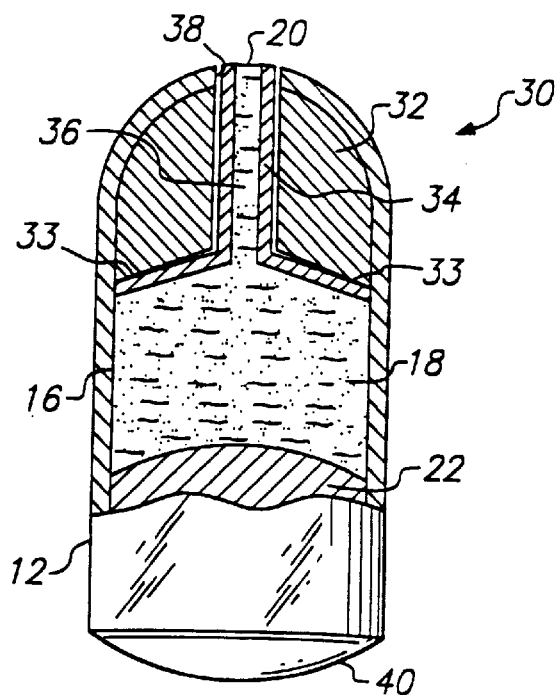
FIG. 2 is a partial cross-sectional view of another embodiment of an improved ruminal delivery device and barrier means according to the present invention.

FIG. 2 illustrates another embodiment of a ruminal delivery device 30, which has a semipermeable cup 12, an internal compartment 16 (partially shown), bore 36 formed in density element 32, drug formulation 18, expandable driving member 22, density element 32, and impermeable barrier means 34. Device 30 differs from device 10 mainly by having the density element 32 positioned near the exit orifice 20 and being provided with a bore 36 extending through the density element to provide contact between drug formulation 18 and the exterior through exit orifice 20.

Barrier means 34, also having a bore therethrough, is placed in the bore 36 and otherwise between the density element and the drug formulation throughout the interface between the two so that there is no contact between them, to provide a barrier for keeping evolved gases from passing into and displacing the drug formulation.

Figure 6:
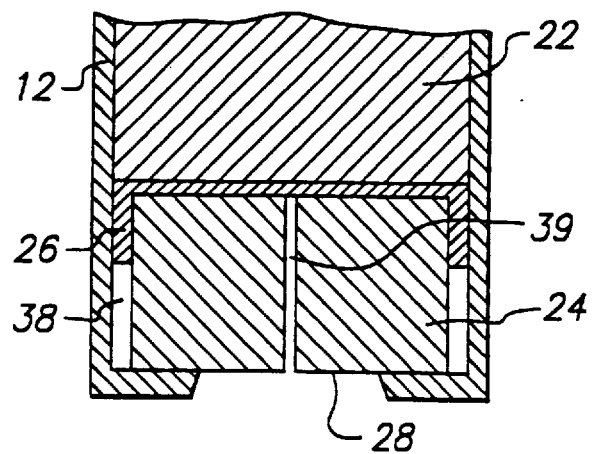
FIG. 6 is an enlarged cross-sectional view of a portion of an improved delivery device showing yet another embodiment of a barrier means.

In a presently preferred embodiment, there is a space or vent 38 between the density element 32 and the barrier means 34 for providing a channel for the evolved gas to vent to the outside of the device. This vent 38 may be provided in any of a number of ways known to the art such as, for example, having the barrier means 34 being in contact with the density element 32 in only a portion of the interface between them, as illustrated in device 30 at point 33. This is also illustrated in FIG. 6, where the barrier means 26 is in contact with only a portion of the density element 24 to provide vent 38. Vent 38 may alternatively be provided by, for example, one or more protrusions extending from either the density element or the barrier means, or both, to separate apart the density element and the barrier; or by one or more grooves present on the interface surface of either the density element or the barrier means, or both. The number of protrusions or grooves is not critical and may be from 1 to 300 or more. In a further alternative embodiment, vents, bores or channels are formed within the density element (by drilling, molding or other means known in the art) and extending through the density element to the exterior environment. This is illustrated in FIG. 6 where bore or vent 39 extends through density element 24 to allow evolved gases to escape to the environment at bottom end 28. Bore or vent 39 may extend completely through the density element, as shown, or it may extend only partially through the density element. The number of vents or bores is not critical and may be from 1 to 50 or more. Other ways of providing a venting means are known or can be determined without undue experimentation by those skilled in the art.

Figure 3:
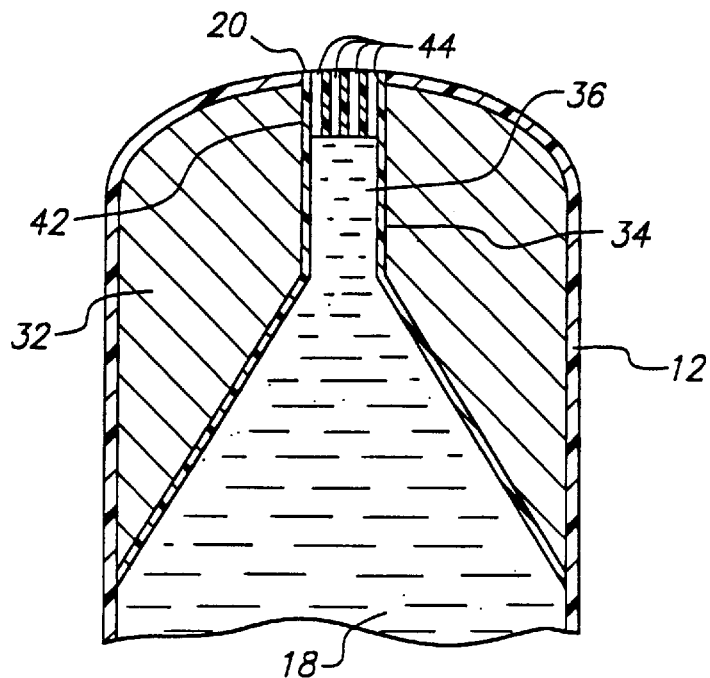
FIG. 3 is an enlarged cross-sectional view of a portion of an improved delivery device showing yet another embodiment of a barrier means, including an exit port screen, according to the present invention.

In certain uses of a ruminal delivery device, it is desirable to have a screen across the exit orifice for keeping external matter out of the device or for providing a back-pressure for improved drug delivery from the device. Capscreens are disclosed in U.S. Pat. Nos. 4,872,873, 5,122,128 and 5,213,809, the disclosures of which are incorporated herein by reference. In one contemplated embodiment of the present invention, shown in FIG. 3, an exit port screen 42 is incorporated into the barrier means 34 of the present invention. Exit port screen 42 is located at that end of barrier means 34 which is adjacent to the exit orifice 20 of the device and integral with the exit orifice. Exit port screen 42 may, optionally, extend within at least a portion of bore or passageway 36 (shown). Exit port screen 42 covers the exit orifice and has a plurality of screen passageways 44 extending through it for allowing passage of the drug formulation 18 to the external environment. The number of screen passageways 44 is not critical and will depend on the use contemplated for the exit port screen 42, the drug formulation to be delivered, and other considerations pertinent to the particular contemplated use, as is taught in the above cited patents, previously incorporated by reference.

Figure 4:
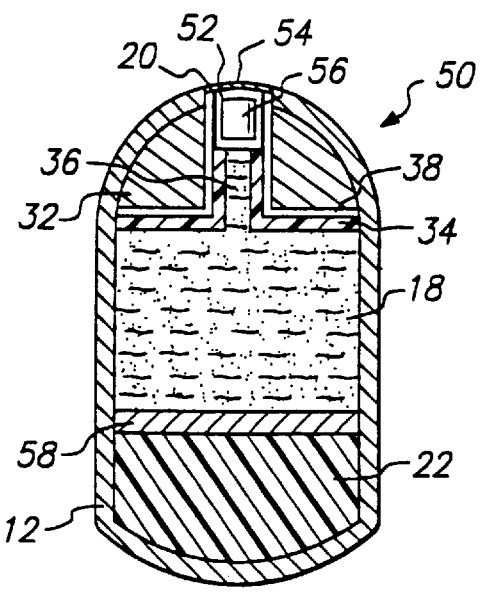
FIG. 4 is a cross-sectional view of a different embodiment of an improved delivery device and a barrier means, including means for maintaining a loading dose tablet, according to the present invention.

In other contemplated uses of a ruminal delivery device, it may be desirable to include a loading dose for providing immediate delivery of a drug during the period of start-up of the device itself. See U.S. Pat. No. 5,045,082, the disclosure of which is incorporated herein by reference. In one embodiment of the present invention, device 50 as shown in FIG. 4, a loading dose chamber 52 is incorporated into the barrier means 34 adjacent to and integral with the exit orifice 20 and the bore or passageway 36. Loading dose chamber 52, together with retaining means 54, is designed to retain a loading dose 56 which contains a formulation for release of drug or other therapeutic agent. The retaining means 54 which covers the loading dose chamber 52 functions to keep the loading dose 56 as an integral part of the dispensing device 50 while allowing consistent dispersion of the loading dose to the external environment over time, as is taught in the above cited patent, previously incorporated by reference. Evolved gases which enter vent 38 are also released through the retaining means, which extends from the loading dose chamber to cover the vent 38 where it opens to the external environment.

In a presently preferred embodiment of the delivery device herein, a moveable partition layer 58 is present between the drug formulation 18 and the expandable driving member 22 to maintain the separate identity of the two components and to assist in the expulsion of the drug formulation from the device into the external environment. Partition layers are well known in the art and are further described in, for example, U.S. Pat. Nos. 4,772,474 and 4,844,984, the disclosures of which are incorporated herein by reference.

The barrier means of this invention are characterized by being essentially impermeable to any gases, and in particular to hydrogen gas, which are evolved as part of the corrosion process of metallic density elements. By "essentially impermeable" is meant that the barrier material is not permeable to such gases at all, or that the gases permeate the material in only a negligible amount, of no greater than about $20\times10^{-10}$ cm/sec-cmHg. The materials suitable for the barrier means are any materials that are essentially impermeable to gases and that are additionally inert to the drug formulation, the density element and the other components of the delivery device. Such characteristics are known in the art or can be determined without undue experimentation. Materials may be selected from, but are not limited to, polyvinyl alcohol; polypropylene; cellulose; cellulose esters; Delrin®; fluorocarbon polymers; polyamides; polyesters; polyolefins; noncorrosive-metals such as stainless steel; nylon; and the like.

The barrier means can be manufactured according to processes well known in the polymer and plastic arts, such as by injection molding, compression molding, casting, mechanical machining, and the like. Where venting means are not present between the density element and the barrier means, the barrier means may be a coating applied directly onto the surface of the density element by coating processes as are known in the art. When the barrier means is an insert, it is sized and shaped to be placed between the density element and the other components within a ruminal drug delivery device.

Figure 5:
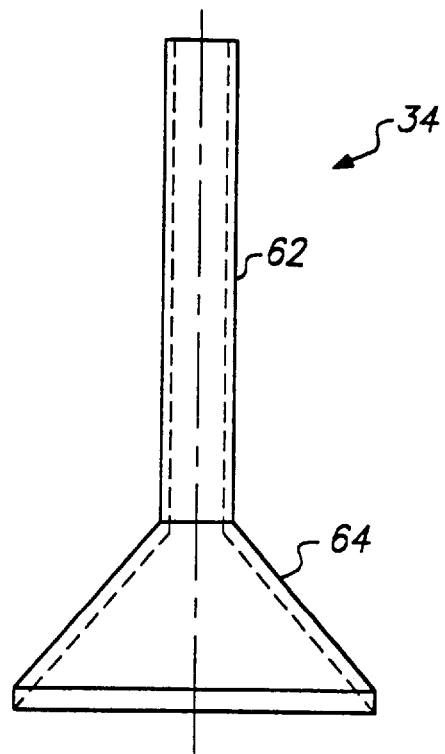
FIG. 5 is a side view of one embodiment of the gas-impermeable barrier means of the present invention.

A representative embodiment of an insert barrier article of the present invention is shown in FIG. 5. FIG. 5 illustrates an insert 34 (which is shown in FIG. 2 in cross-section positioned in a ruminal delivery device). Barrier insert 34 is funnel-shaped, having a circular cross-section along its longitudinal axis. Barrier insert 34 includes a narrow neck portion 62 to fluidly connect the drug composition 18 with the environment of use and a frustro-conically shaped separating portion 64 for separating the density element from the drug formulation. Portions of the barrier insert 34 are sized and shaped to closely fit the density element (32 in FIG. 2) while other portions being positioned to form a channel for escaping gases (vent 38 in FIG. 2). In a presently preferred embodiment, the barrier insert of the present invention is manufactured of Delrin® ((polyoxymethylene) acetyl resin homopolymer; DuPont). The material should not shrink or oxpand when introduced into the ruminal environment.

It was believed that the tight initial fit of the density element 32 within the cup 12 would provide sufficient means to retain the elements inserted within the compartment 16. It was also believed that as the cup absorbed fluid, it would swell, decreasing the inner diameter of the cup swelled. This constriction in the inner diameter of the cup 12 would provide additional means for the cup to engage and retain the density element 32 within the compartment 16. It was discovered, however that sometimes the inner diameter of the semipermeable cup 12 increased after exposure to fluid, reducing the cup's ability to firmly engage or grasp the density element 32.

Furthermore, it was discovered that with cup constructions where the cup wall was crimped around the inserted density element, the crimped cup was not always able to retain the internal elements, e.g., the density element 32 the drug formulation 18 and the expandable driving member 22, within the internal compartment. It was discovered that as the expandable driving member 22 expanded upon exposure to the fluid imbibed across the semipermeable cup 12, it pushed against the density member 32, which in turn, sometimes forced against the crimped portion of the wall, straightening it. This allowed the density element 32 to pass out from the compartment and into the environment of use.

Figure 8:
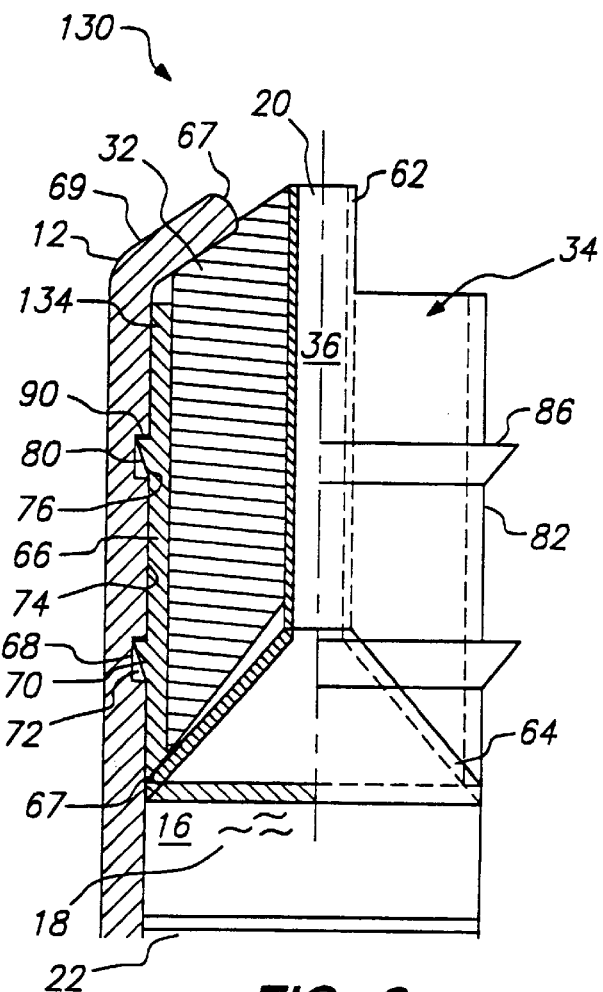
FIG. 8 is an enlarged, fragmented, cross-sectional side view of one embodiment of the gas-impermeable barrier means including a coupler of the present invention.

According to this invention, in the embodiment illustrated in FIG. 8, ruminal delivery device 130 includes another embodiment of a ruminal delivery device 130 which has additional means 80, 90 for securing the density element 32 therein. In ruminal delivery devices having a construction similar to device 30 (FIG. 4), a semipermeable cup 65, with open end 67, an internal compartment 16 defined therein (partially shown), exit orifice 20, drug formulation 18, expandable driving member 22, density element 32, and impermeable barrier means 134. Adjacent the exit orifice 20, the open end 69 of the semipermeable cup 65 is crimped over to retain the density element 32 within the internal compartment 16. The barrier insert 34 includes a coupling sleeve 66, extending between the semipermeable cup 65 and the density element 32. The coupling sleeve 66 transfers, to the wall, the pressure generated by the expandable driving member 22, reducing the pressure applied to the crimped portion of the wall. In this embodiment, the sleeve 66 is a cylindrical extension joined with the outer-most edge 67 of the frustro conical portion 64, extending towards the exit orifice 20. Sleeve 66 is sized to surround tightly engage and snugly fit the density element 32. In the preferred embodiment, the density element 32 is force fitted within the sleeve 66 to be snugly retained therein. Sleeve 66 is provided with one or more coupling means 68 so that the tightly engaged density element 32 is engaged with semipermeable cap 65. Thus, the tensile strength of the coupling means, in combination with that of the crimped portion 69 of the cup, is greater than the osmotic pressure generated by the expandable driving member, keeping the density element 32 within the cup. This prevents the sleeve 66, and thus the density element 32 retained therein, from being expelled from the device even if the crimped portion of the semipermeable cup is straightened.

The coupler 68 includes a projection 70, positioned and sized to be received within a receiving depression 72. In this embodiment, the receiving depression 72 is defined within the inside surface 74 of the cup 65. The corresponding projection 70 extends radially outward from the outside surface 76 of the sleeve 66. In this particular embodiment, the projection 70 includes an outwardly sloping face 80 which terminates in an abutting face 86, perpendicular to the longitudinal axis of the device 10 to provide an abutting surface to engage with the side 90 of the receiving depression 72. In one embodiment, the receiving depression 72 is an annular, circumferential trough defined within the inside surface 74 of the semipermeable cup 65.

Barrier means 134 is preferably bonded to the density element 32. Typical methods of direct bonding include heat sealing, adhesive sealing, solvent sealing, ultrasonic sealing, radio frequency sealing, or spin welding (also know as friction heating to weld) methods. Furthermore, since the density element 32 closely fits within the cup shaped barrier 34, the density element is prevented from moving about within the internal compartment 16 and towards the open end of the cup.

Figure 9:
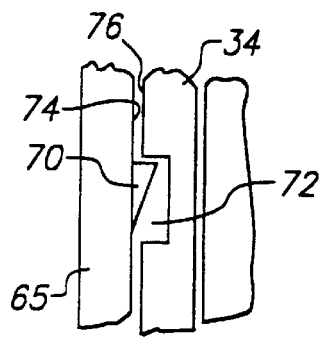
FIG. 9 is an enlarged, fragmented, cross-sectional side view of another embodiment of the gas-impermeable barrier means including a coupler of the present invention.

As shown in FIG. 9, it is also contemplated that the receiving depression 72 may also be defined within the outside surface 76 of the impermeable barrier 34 and the projection 70 extends radially inwards from the inside surface 74 of the cup 65 to separate and immobilize the density element 32 relative to the cup 65.

The following examples are illustrative of the present invention. They are not to be construed as limitations of the scope of the invention. Variations and equivalents of these examples will be apparent to one skilled in the art in light of the present disclosure, the drawings, and the claims herein. All percentages are weight-weight percent, and all temperatures are in degrees Celsius, unless otherwise noted.

EXAMPLE 1

An improved ruminal delivery device according to the present invention is prepared as follows.

A semipermeable wall was prepared by sizing and then mixing together 50.5 g cellulose acetate butyrate having a butyryl content of 17% and an acetyl content of 29% (Eastman), 17.5 g cellulose acetate having an acetyl content of 39.8% (Eastman), 22.0 g triethyl citrate (Citroflex-4®, Morflex, Inc.), 6.0 g tributyl citrate (Citroflex-2®, Morflex, Inc.), and 4.0 g polyethylene glycol having a molecular weight of 400 (PEG 400, Union Carbide). After mixing for 20 minutes, the material was transferred to the feed hopper of an injector molder equipped with a suitable mold to produce a cellulosic membrane cup weighing 10.1 g and having the following dimensions: 7.9 cm height, 2.5 cm width, and wall thickness of 0.17 cm.

An osmotic expandable driving member was prepared by blending together 60.3 g sodium salt of polyacrylic acid having a MW of 3,000,000 (Sodium Carbomer® 934P, B.F. Goodrich Chemical), 0.9 g polyvinylpyrrolidone (PVP), 0.9 g magnesium stearate, 12.9 g water, and 25 g sodium chloride. 8.41 Grams of the blend was compressed under 10 tons of force to form tablets which conform to the internal diameter of the membrane cups prepared above. One of the compressed osmotic tablets was inserted into the membrane cup.

A placebo "drug" formulation was prepared by melting a microcrystalline wax (Multiwax® X145A; Witco Chemical Co.) and, with the temperature maintained at 68° C., delivering 11.5 g (about 12.8 mL) of the wax to the membrane cup assembly over the osmotic tablet.

A sintered iron density element was prepared, having a 5.1 mm diameter bore therethrough and shaped generally as illustrated in FIG. 2 and of a size for placement in the membrane cup.

A barrier insert as illustrated in FIG. 5 was prepared by machining a funnel-shaped insert from Delrin® in the shape and dimensions set out in FIG. 5 to fit into the inside of the density element with about 7 mil (0.18 mm) clearance between the insert and most of the density element. As shown in FIG. 5, the funnel-shaped barrier insert 34 has a narrow neck portion 62 with a length along the longitudinal axis of about 1.25 inches (3.175 cm), a neck wall thickness of about 0.015 inches (0.0381 cm) and an outside neck diameter of about 0.186 inches (0.472 cm). The separating portion 64 is an angled frustro-conical section with a length along the longitudinal axis of about 0.431 inches (1.095 cm), extending outward from the neck 62 to an outer diameter of about 0.910 inches (2.311 cm). This outermost portion has a thickness along the longitudinal axis of about 0.05 inches (0.127 cm). The angle a defined by the conical portion's face and the orthogonal to the longitudinal axis is about 50°. The total length of the funnel-shaped barrier 34 is about 1.73 inches (4.394 cm).

The barrier insert was placed into the density element so that it is situated next to or against the interior portion of the element, after which the density element was inserted into the open end of the membrane cup assembly and seated against the "drug" formulation. The barrier insert separates the drug formulation from exposure to the density element. The protruding lip of the cup was heated until softened using a hot air gun, and the lip was crimped over the density element, leaving the exit orifice open.

EXAMPLE 2

A ruminal delivery device identical to the device in Example 1 was prepared, except that a barrier insert was not placed into the density element, resulting in a prior art ruminal bolus having an untreated density element placed in contact with drug formulation.

In the same manner, a prior art delivery device was prepared having an impregnated density element and no barrier insert. The density element was impregnated during manufacture with microcrystalline wax Multiwax 180M, following the procedures of U.S. Pat. No. 5,206,024.

EXAMPLE 3

The delivery device of the present invention of Example 1 was compared in vitro, with the prior art devices of Example 2 to compare delivery profiles and presence or absence of gas within the drug formulation, as follows.

Figure 7:
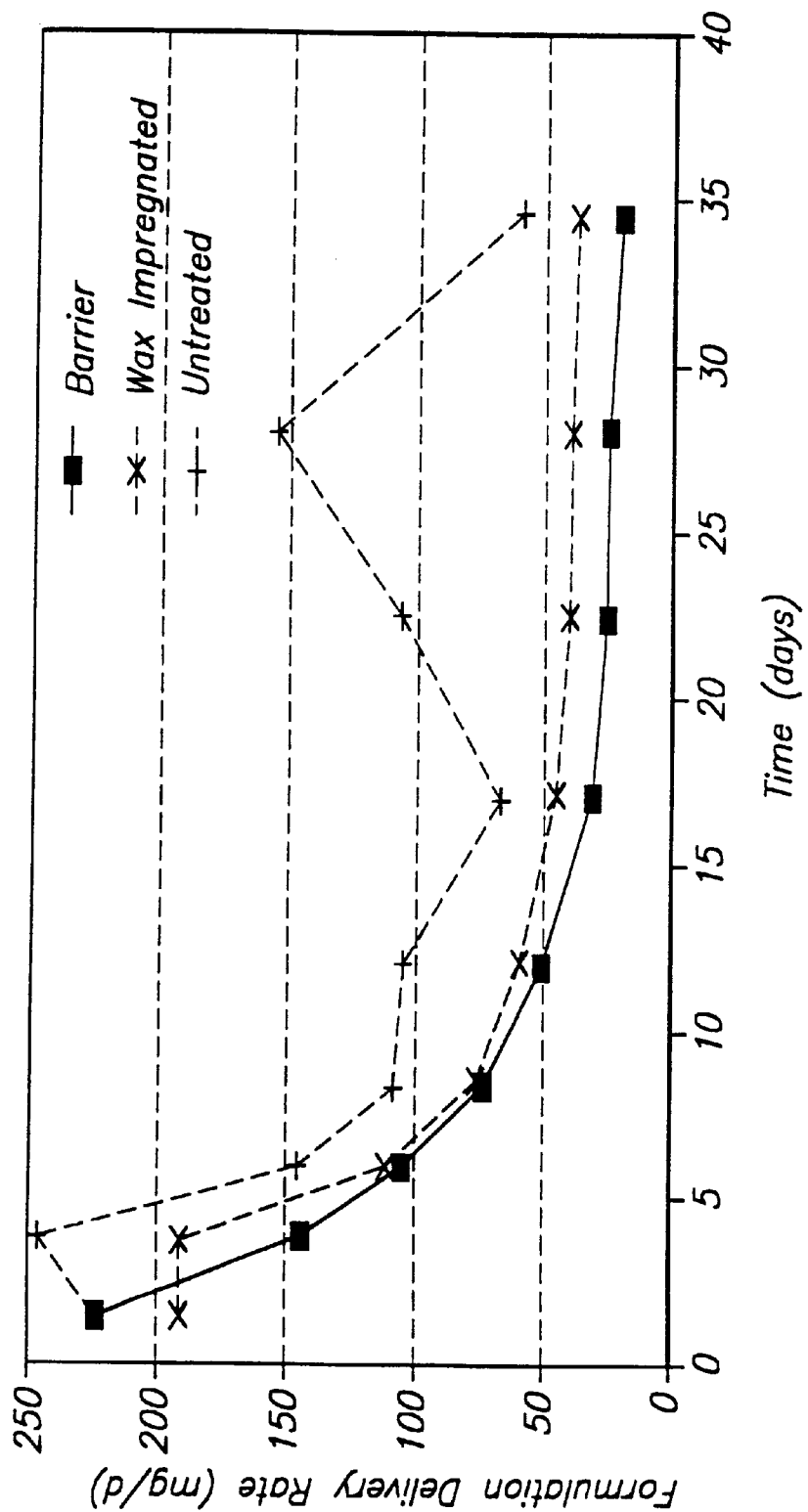
FIG. 7 is a graph illustrating the release rate of devices of the present invention in comparison with release rates of prior art devices.

The devices (n=8) were placed in deionized water and maintained at ruminant body temperature. Material which extruded from the devices was removed periodically and weighed to determine the release rate from each of the devices. The comparative averaged release rates for the devices are presented in FIG. 7.

At the end of the testing, each of the devices was cut open to determine the presence or absence of voids caused by gas bubbles. Out of the eight devices in each set, there were severe voids (15–25 mm) in three of the untreated devices, there were minor voids (2–5 mm) in three of the wax-impregnated devices, and there were no voids whatever in any of the devices of the invention having barrier inserts.

EXAMPLE 4

A delivery device for the delivery of ivermectin is prepared as described in Example 1, except as follows.

After the osmotic expandable tablet is inserted into the membrane cup, two grades of microcrystalline wax (49 g Multiwax® 180M and 49 g Multiwax® X145A) and 2 g Cab-O-Sil® (colloidal silicone dioxide, Cabot Corp.) are mixed together, and the mixture is heated to 85° in a hot-melt tank pump. 3.0 Grams (about 3.3 mL) of the wax mixture is poured into the membrane cup in laminated arrangement above the osmotic expandable tablet to form a partition layer.

An ivermectin drug formulation is prepared as follows. 831 g Multiwax X145A and 20 g Cab-O-Sil are melted, after which the temperature is adjusted to 80° C. Ivermectin (149 g) is added, using a high sheer mixing apparatus. The temperature of the formulation is maintained at 68° C. while 8.5 g (about 9.5 mL) of the formulation is delivered to the membrane cup assembly over the partition layer.

The barrier insert and the density element are then added as in Example 1 to give an ivermectin ruminal bolus.

EXAMPLE 5

A delivery device for the delivery of ivermectin is prepared as described in Example 1, except as follows.

A cup-shaped polycarbonate barrier insert as illustrated in FIG. 8 was prepared by machining an insert from Delrin® in the shape and dimensions set out in FIG. 8 to received therein the density element with about 7 mm (0.18 mil) clearance between the insert and most of the density element to form a channel for escaping gases (similar to vent 38 shown in FIG. 2).

As shown in the embodiment illustrated in FIG. 8, the neck 62 and separating portion 64 have the same dimensions as disclosed with respect to insert barrier 34, illustrated in FIG. 5. In addition, sleeve 66, extends along the device's longitudinal axis, and has an inside diameter sized to snugly engage with a density element 34 having an outside diameter of 0.910 inches (2.3114 cm). The projection 72 extends outward from a first diameter. The sloping face is angled relative to the surface defined by the first diameter for a distance along the device's longitudinal axis. The receiving depression is an annular trough cut within the inside surface of the well.

What is claimed is:

1. An insert for use in combination with a ruminal drug delivery device having a semipermeable cup defining a compartment, an osmotic expandable driving member, a drug formulation containing a drug to be dispensed, a density element, and exit means for fluidly connecting the drug formulation with the environment of use, the insert being essentially gas-impermeable and being sized and shaped to be placed between a density element and the drug formulation.

2. An insert as set forth in claim 1, wherein the insert is retained within the compartment and the density element retained within the insert.

3. An insert according to claim 1 which comprises a material selected from the group consisting of polyvinyl alcohol, polypropylene, cellulose, cellulose esters, acetyl resins, fluorocarbon polymers, polyamides, polyesters, polyolefins, nylon, and noncorrosive metals.

4. An insert according to claim 1, which further comprises venting means.

5. An insert according to claim wherein the venting means is selected from the group consisting of one or more protrusions, one or more grooves, one or more bores, and combinations thereof.

6. An insert according to claim 1, which further comprises an exit port screen.

7. An insert according to claim 1 which further comprises a loading dose chamber and a loading dose.

* * * * *

UNITED STATES PATENT AND TRADEMARK OFFICE
CERTIFICATE OF CORRECTION

PATENT NO. : 5,997,902
DATED : December 7, 1999
INVENTOR(S) : Frederick H. Maruyama et al It is certified that error appears in the above-identified patent and that said Letters Patent is hereby corrected as shown below:

In claim 5, line 1, kindly insert "4" after "claim"

Signed and Sealed this

Seventh Day of November, 2000

Attest:

Q. TODD DICKINSON

*Attesting Officer*     *Director of Patents and Trademarks*